(12) United States Patent
Lentz et al.

(10) Patent No.: US 10,221,323 B2
(45) Date of Patent: Mar. 5, 2019

(54) MICROCAPSULES HAVING DUAL REAGENTS SEPARATED BY THE CAPSULE WALL AND METHODS FOR MAKING SAME

(71) Applicant: Microtek Laboratories, Inc., Dayton, OH (US)

(72) Inventors: Carl M Lentz, Waynesville, OH (US); Kayla L. M. Ryan, Fairborn, OH (US)

(73) Assignee: Microtek Laboratories, INC., Dayton, OH (US)

( * ) Notice: Subject to any disclaimer, the term of this patent is extended or adjusted under 35 U.S.C. 154(b) by 0 days.

(21) Appl. No.: 15/646,478

(22) Filed: Jul. 11, 2017

(65) Prior Publication Data

US 2018/0010013 A1    Jan. 11, 2018

Related U.S. Application Data

(60) Provisional application No. 62/360,672, filed on Jul. 11, 2016, provisional application No. 62/419,325, filed on Nov. 8, 2016.

(51) Int. Cl.

| | |
|---|---|
| *C09D 5/14* | (2006.01) |
| *A01N 25/28* | (2006.01) |
| *A01N 59/06* | (2006.01) |
| *A01N 59/16* | (2006.01) |
| *A01N 59/20* | (2006.01) |
| *A01N 59/26* | (2006.01) |
| *B01J 13/22* | (2006.01) |
| *C09D 133/00* | (2006.01) |
| *C09D 161/28* | (2006.01) |
| *C09D 179/04* | (2006.01) |
| *C09K 5/06* | (2006.01) |
| *B01J 13/08* | (2006.01) |
| *C09D 5/00* | (2006.01) |
| *C09F 9/00* | (2006.01) |
| *B01J 13/02* | (2006.01) |
| *B01J 13/14* | (2006.01) |
| *F28D 20/02* | (2006.01) |
| *C09D 7/61* | (2018.01) |
| *C09D 7/40* | (2018.01) |
| *C09D 161/34* | (2006.01) |
| *C08G 14/08* | (2006.01) |

(52) U.S. Cl.
CPC ............... *C09D 5/14* (2013.01); *A01N 25/28* (2013.01); *A01N 59/06* (2013.01); *A01N 59/16* (2013.01); *A01N 59/20* (2013.01); *A01N 59/26* (2013.01); *B01J 13/02* (2013.01); *B01J 13/08* (2013.01); *B01J 13/14* (2013.01); *B01J 13/22* (2013.01); *C09D 5/00* (2013.01); *C09D 7/61* (2018.01); *C09D 7/66* (2018.01); *C09D 133/00* (2013.01); *C09D 161/28* (2013.01); *C09D 161/34* (2013.01); *C09D 179/04* (2013.01); *C09F 9/00* (2013.01); *C09K 5/063* (2013.01); *F28D 20/023* (2013.01); *C08G 14/08* (2013.01)

(58) Field of Classification Search
None
See application file for complete search history.

(56) References Cited

U.S. PATENT DOCUMENTS

| | | | |
|---|---|---|---|
| 6,075,072 A | 6/2000 | Guilbert et al. | |
| 6,518,330 B2 | 2/2003 | White et al. | |
| 6,858,659 B2 | 2/2005 | White et al. | |
| 7,115,764 B2 | 10/2006 | Barron et al. | |
| 7,550,200 B2 * | 6/2009 | Hart | A01N 43/80 424/408 |
| 7,919,184 B2 | 4/2011 | Mohapatra et al. | |
| 8,829,082 B2 | 9/2014 | Boday et al. | |
| 2010/0297446 A1 | 11/2010 | Oxley et al. | |
| 2013/0324639 A1 * | 12/2013 | Boday | B29C 73/22 523/202 |
| 2014/0197355 A1 | 7/2014 | Ram et al. | |
| 2015/0158003 A1 | 6/2015 | Virgallito et al. | |
| 2015/0190774 A1 | 7/2015 | Phipps et al. | |
| 2017/0247626 A1 | 8/2017 | Ng et al. | |

FOREIGN PATENT DOCUMENTS

| | | |
|---|---|---|
| WO | 2003055588 A1 | 10/2003 |
| WO | 2015074039 A2 | 5/2015 |
| WO | 2015157354 A1 | 10/2015 |

OTHER PUBLICATIONS

Blaiszik et al., "Self-Healing Polymers and Composites", Annu. Rev. Mater. Res., 2010, 40:179-211.
Brochu et al., "Microencapsulation of 2-octylcyanoacrylate tissue adhesive for self-healing acrylic bone cement", J Biomed Mater Res B Appl Biomater. Oct. 2012;100(7):1764-72. doi: 10.1002/jbm.b.32743. Epub Jul. 18, 2012.
Cao et al., "Properties evaluation and applications of thermal energystorage materials in buildings", Renewable and Sustainable Energy Reviews, vol. 48, Aug. 2015, pp. 500-522.
Ge et al., "Stability and optimum polymerized condition of polysiloxane-polyacrylate core/shell polymer", Advances in Polymer Technology, vol. 29, Issue 3, 161-172, 2010, Abstract only.
Gray et al., "Determination of microcapsule physicochemical, structural, and mechanical properties", Particuology, vol. 24, 2016, pp. 32-43, Abstract only.

(Continued)

*Primary Examiner* — Robert T Butcher
(74) *Attorney, Agent, or Firm* — FisherBroyles, LLP; Susan M. Oiler

(57) ABSTRACT

Ruptureable, dual reagent mono-capsules are disclosed that have a core composition, which includes a first reagent, encapsulated within a polymer wall, and a shell connected to an exterior surface of the polymer wall by a surfactant. The shell is made from a second reagent that is chemically bonded to the surfactant by a chemical electrostatic interaction. Upon rupture of the polymer wall of the mono-capsule, the first reagent and the second reagent chemically react with one another to form a reaction product.

20 Claims, 8 Drawing Sheets

(56) References Cited

OTHER PUBLICATIONS

He et al., "New approach for sol-gel synthesis of microencapsulated n-octadecane phase change material with silica wall using sodium silicate precursor", Energy, 67:223-233, 2014 Abstract only.

Kamdem et al., "Optimization Process by Complex Coacervation of Fish Oil Using Gelatin/SDS/NaCMC and Secondary Coating Application with Sodium Polyphosphate", IJSBAR. 2014, 17(1):74-94.

Liao et al., "Preparation of Organic/Inorganic Hybrid Polymer Emulsions with High Silicon Content and Sol-gel-derived Thin Films", Chinese Journal of Chemical Engineering, 18(1):156-163, 2010 Abstract only.

Long et al., "Organic-inorganic double shell composite microcapsules", Chemical Communications, 46:1718-1720, 2010.

Nomura, "Microencapsulation of Metal-based Phase Change Material for High-temperature Thermal Energy Storage", Scientific Reports, 5:9117, DOI:10.1038/srep09117.

Onder et al., "Encapsulation of Phase Change Materials by Complex Coacervation to Improve Thermal Performances of Woven Fabrics", Thermochimica Acta. 2008, 467, 63-72 Abstract only.

Pan et al., "Preparation, characterization and thermal properties of micro-encapsulated phase change materials",Solar Energy Materials and Solar Cells, 98:66-70, 2012.

Wang et al., "Highly efficient and selective infrared absorption material based on layered double hydroxides for use in agricultural plastic film" Applied Clay Science. 53( )4):592-597, 2011, Abstract only.

Wilson et al., "Self-Healing Polymers", Encyclopedia of Polymer Science and Technology, 2010, John Wiley & Sons, Inc., 33 pages.

Yang et al., "Microencapsulation of Isocyanates for Self-Healing Polymers", Macromolecules, 2008, 41 (24), pp. 9650-9655, DOI: 10.1021/ma801718v Abstract only.

Yang et al., "Self-healing composites: A review", Cogent Engineering, 2015, 2:1075686, 28 pages.

Yu et al., "Self-Assembly Synthesis of Microencapsulated n-Eicosane Phase-Change Materials with Crystalline-Phase-Controllable Calcium Carbonate Shell", Energy Fuels, 2014, 28 (5), pp. 3519-3529, Abstract only.

Yu et al., "Microencapsulation of n-octadecane phase change material with calcium carbonate shell for enhancement of thermal conductivity and serving durability: Synthesis, microstructure, and performance evaluation", Applied Energy, 114:632-643, 2014, Abstract only.

Zhang et al., "Design and fabrication of dual-functional microcapsules containing phase change material core and zirconium oxide shell with fluorescent characteristics", Solar Energy Materials and Solar Cells, 133:56-68, 2015, Abstract only.

Crespy et al., "Self-Healing for Anticorrosion Based on Encapsulated Healing Agents", Based on Encapsulated Healing Agents. Advances in Polymer Science, 273, 219-245. doi:10.1007/12_2015_342. Abstract only.

Derakhshan et al., "Morphology and production mechanism of the functionalized carboxylate alumoxane micro and nanostructures", Powder Technology, 2012, 225:156-166 Abstract only.

Di Credico et al., "An efficient method for the output of new self-repairing materials through a reactive isocyanate encapsulation", European Polymer Journal, 2013, 49(9):2467-2476 Abstract only.

Haghayegh et al., "Preparation of microcapsules containing multi-functional reactive isocyanate-terminated-polyurethane-prepolymer as healing agent, part II: corrosion performance and mechanical properties of a self healing coating", RSC Advances, 2016, 56(6):50874-50886 Abstract only.

Haghayegh et al., "Microcapsules containing multi-functional reactive isocyanate-terminated polyurethane prepolymer as a healing agent. Part 1: synthesis and optimization of reaction conditions", J. Mater. Sci., 2016, 51:3056-3068 Abstract only.

Hia et al., "Self-Healing Polymer Composites: Prospects, Challenges, and Applications", Polymer Reviews, 2016, 56:225-261 Abstract only.

Jin et al., "Self-healing thermoset using encapsulated epoxy-amine healing chemistry", Poylmer, 2012, 1-7, doi:10.1016/j.polymer.2011.12.005.

Kopec et al., "Self-healing epoxy coatings loaded with inhibitor-containing polyelectrolyte nanocapsules", Progress in Organic Coatings, 2015, 84:97-106 Abstract only.

Konuklu et al., "Microencapsulation of a fatty acid with Poly(melamine-urea-formaldehyde)", Energy Conversion and Management, 2014, 80:382-390 Abstract only.

Nesterova et al., "Synthesis of durable microcapsules for self-healing anticorrosive coatings: A comparison of selected methods", Progress in Organic Coatings, 2011, 70(4):342-352 Abstract only.

Samadzadeh et al., "Tung oil: An autonomous repairing agent for self-healing epoxy coatings", Progress in Organiz Coatings, 2011, 70(4):383-387 Abstract only.

Ullah et al., "The Potential of Microencapsulated Self-healing Materials for Microcracks Recovery in Self-healing Composite Systems: A Review", Polymer Reviews, 2016, 56(3):429-485 Abstract only.

Vogelson et al., "Inorganic-Organic Hybrid and Composite Resin Materials Using Carboxylate-Alumoxanes as Functionalized Cross-Linking Agents", Chem. Mater., 2000, 12 (3), pp. 795-804, DOI: 10.1021/cm990648e Abstract only.

WO, International Search Report and Written Opinion, Application No. US2017/41505, Filed Jul. 11, 2017, (11 Pages).

* cited by examiner 60x magnification 10x magnification

MICROCAPSULES HAVING DUAL REAGENTS SEPARATED BY THE CAPSULE WALL AND METHODS FOR MAKING SAME

RELATED APPLICATIONS

This application claims the benefit of U.S. Provisional Application No. 62/360,672, filed Jul. 11, 2016, which is incorporated herein by reference, and the benefit of U.S. Provisional Application No. 62/419,325, filed Nov. 8, 2016, which is incorporated herein by reference.

TECHNICAL FIELD

The present application relates to a dual reagent microcapsule with a first reagent in the core composition and a second reagent tethered to the polymer wall of the microcapsule, where the first reagent and second reagent chemically react together to form a reaction product once the microcapsule ruptures.

BACKGROUND

Microcapsules can be constructed of various types of wall or shell materials to house varying core material for many purposes. The encapsulation process is commonly referred to as microencapsulation. Microencapsulation is the process of surrounding or enveloping one substance, often referred to as the core material, within another substance, often referred to as the wall, shell, or capsule, on a very small scale. The scale for microcapsules may be particles with diameters in the range between 1 μm and 1000 μm that consist of a core material and a covering shell. The microcapsules may be spherically shaped, with a continuous wall surrounding the core, while others may be asymmetrical and variably shaped.

General encapsulation processes include emulsion polymerization, bulk polymerization, solution polymerization, and/or suspension polymerization and typically include a catalyst. Emulsion polymerization occurs in a water/oil or oil/water mixed phase. Bulk polymerization is carried out in the absence of solvent. Solution polymerization is carried out in a solvent in which both the monomer and subsequent polymer are soluble. Suspension polymerization is carried out in the presence of a solvent (usually water) in which the monomer is insoluble and in which it is suspended by agitation. To prevent the droplets of monomers from coalescing and to prevent the polymer from coagulating, protective colloids are typically added.

Through a selection of the core and shell material, it is possible to obtain microcapsules with a variety of functions. This is why microcapsules can be defined as containers, which can release, protect and/or mask various kinds of active core materials. Microencapsulation is mainly used for the separation of the core material from the environment, but it can also be used for controlled release of core material in the environment. Microcapsule walls can also act as a barrier, separating a two-component system, where one constituent is in the core and the other is in the environment surrounding the capsule, such as being within a matrix in which the capsules are located. A disadvantage to a capsule/matrix system is that they are typically not cost effective because the matrix requires more material of the second reagent or catalyst to be present than is actually necessary for a typical reaction to occur. Furthermore, an even dispersion of the capsules in the matrix (or medium) is required, and is not easily achieved when considering the differences in density of the materials and/or the size of the capsule. Furthermore, often times a specific stoichiometry of reagents is required, and having one reagent as the matrix would limit the number of reactions that can be carried out.

Another way to separate two components is by synthesizing two different capsules, one with a first reagent in it and the other with a second reagent in it. When the capsules are ruptured by damage, the intended effect is triggered through the release and reaction of the reagents. After release, the reagent is depleted, leading to a singular local event. The main issue with having two separate capsules is that both capsules would need to be ruptured simultaneously within a reasonable distance from one another in order for a reaction to occur. Furthermore, an even dispersion of the two capsules is required, which is not easily achieved when considering the differences in the density of materials and/or the size of the two capsules.

Since the development of microcapsules, there has been a constant need for improved microcapsules. Further, self-healing formulations have been researched for at least the past decade in an attempt to restore the physical and mechanical integrity of a surface quickly after damage occurs without human intervention. In particular, there is a need to develop a two-component microcapsule system that separates two reagents in a more compact unit, in close proximity until the time is needed for their interaction, especially ones that can provide a self-healing formulation.

SUMMARY

In all aspects, dual reagent mono-microcapsules are disclosed that have a first reagent in the core composition of the capsule and the second reagent tethered to the exterior surface of the polymer wall of the microcapsules by a surfactant. As such, the microcapsules carry the second reagent with them for equal distribution of the first and second reagents throughout a carrier, such as a paint, coating, or the like. Upon rupture of the microcapsules, the two reagents will react with one another and form a reaction product. In one embodiment, the reaction product is a material suitable for self-healing a surface upon which the microcapsules are present.

Described in detail is a method for a two-part reagent microcapsule, where one reagent is located within the capsule wall, this is referred to as the core. The second reagent is tethered to the exterior surface of the capsule wall surface via a surfactant. The material located within and the material located on the outside of the capsules will react with one another upon contact, creating a compound with desired properties. The contact between the two reagents occurs upon rupture of the microcapsules. In one embodiment, the two reagents are selected to form a self-healing reaction product.

In all aspects, ruptureable capsules are disclosed that have a core composition encapsulated within a polymer wall, the core composition comprising a first reagent, and a shell connected to an exterior surface of the polymer wall by a surfactant, the shell comprising a second reagent attracted to the surfactant by a chemical electrostatic interaction. Upon rupture of the polymer wall, the first reagent and the second reagent chemically react with one another to form a reaction product. The rupture of the polymer wall may be by any means, such as mechanical or chemical means, such as a scrape or marring of a surface or as a result of a pH change. The reaction product, after rupture of the capsules, seals the rupture in the capsule and/or seals a feature of a surface upon which the capsules are disposed.

In one embodiment, the second reagent comprises a mineral containing a metal that is available for chemical attraction or bonding to the surfactant, and the first reagent is a carboxylic acid. The metal within the mineral may be aluminum calcium, silver, magnesium, iron, copper, and cobalt, and combinations thereof.

In another embodiment, the second reagent is an inorganic compound forming the shell connected to the exterior surface of the polymer wall, and the inorganic shell is crystalline. Here, the core composition comprises a natural oil, and the inorganic compound is one that catalyzes a reaction of the natural oil.

In all embodiments, regardless of the core composition, the shell can be a discontinuous or a continuous about the polymer wall, the surfactant comprises an ionic surfactant, and the polymer wall comprises melamine formaldehyde, gelatin, cross-linked melamine, resorcinol urea formaldehyde, or acrylic polymer.

In another aspect, methods for surface treating capsules to form an outer shell about the polymer wall of preformed capsules is disclosed. The methods include providing capsules comprising a core composition encapsulated within a polymer wall, mixing an aqueous surfactant and the capsules together under conditions that enables surfactant attachment to an exterior surface of the polymer wall to form a surfactant-capsule intermediate, and then adding a solution of an inorganic compound where a metal therein is available for association with the surfactant. The inorganic compound is added with mixing until the metal of the inorganic compound chemically bonds to the surfactant and forms an outer shell on the polymer wall of the capsules. The method may also include a step of first forming the capsules before mixing with the aqueous surfactant.

In all embodiments, regardless of the core composition inside the polymer wall, the shell attached to the polymer wall can be a discontinuous or a continuous about the polymer wall, the surfactant comprises an ionic surfactant, and the polymer wall comprises melamine formaldehyde, gelatin, cross-linked melamine, resorcinol urea formaldehyde, or acrylic polymer. In one embodiment, the core composition comprises a natural oil, and the inorganic compound is one that catalyzes a reaction of the natural oil. In another embodiment, the core composition comprises a carboxylic acid and the inorganic compound is one that chemically reacts with the carboxylic acid.

In another aspect, self-healing materials are disclosed that have a plurality of the ruptureable capsules disclosed herein in a delivery medium.

DETAILED DESCRIPTION

The following detailed description will illustrate the general principles of the invention, examples of which are additionally illustrated in the accompanying drawings.

As used herein, the term "about" allows a degree of variability in a value or range, for example, within 10% of a stated value or of a stated limit of a range for all embodiments, but within 5% of a stated value or of a stated limit of a range in more preferred embodiments.

Figure 1:
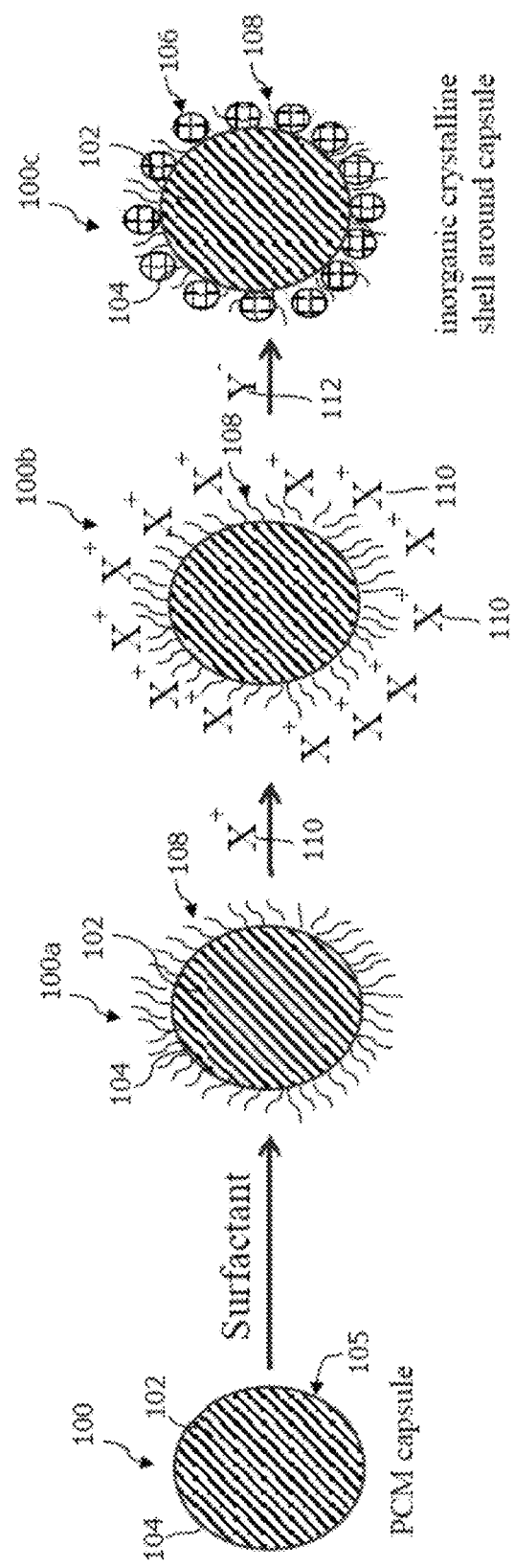
FIG. 1 is a flow diagram of a first embodiment of shell formation on microcapsules, represented as a cross-sectional view.
Figure 2:
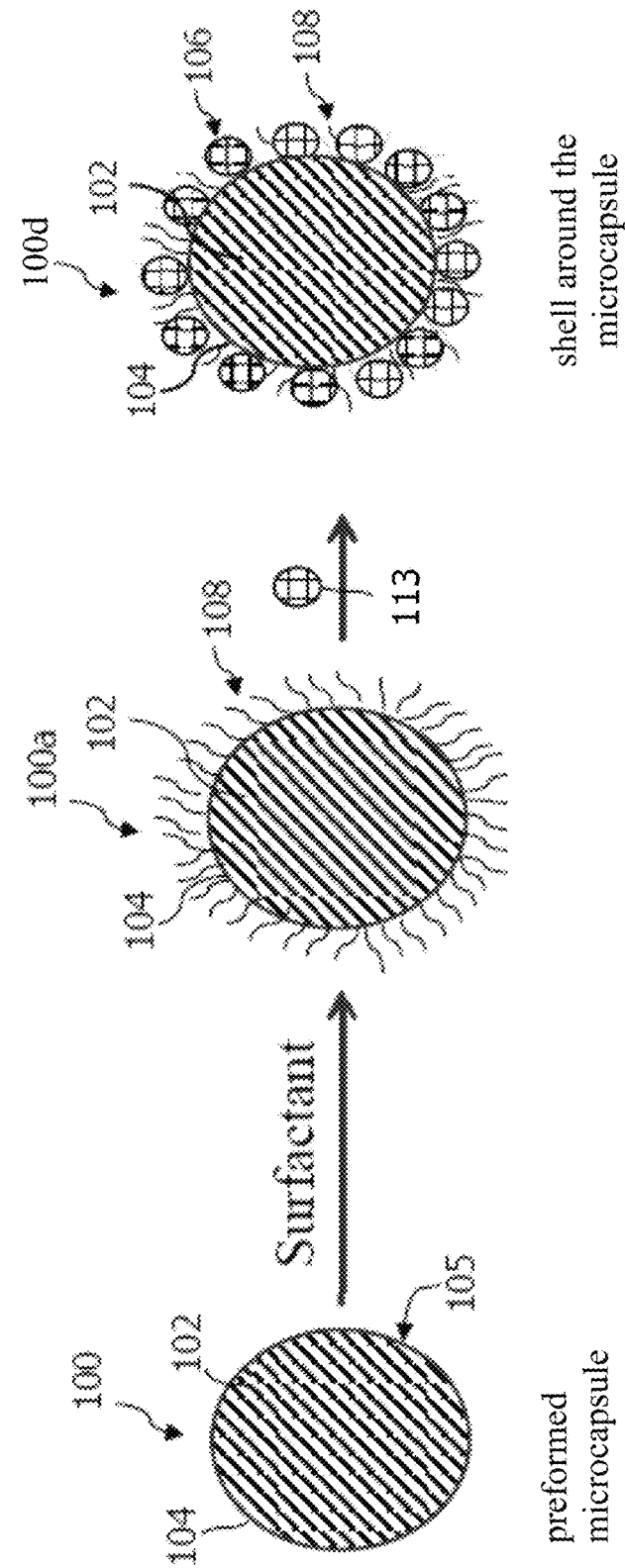
FIG. 2 is flow diagram of a second embodiment of shell formation on microcapsules, represented as a cross-sectional view.
Figure 3:
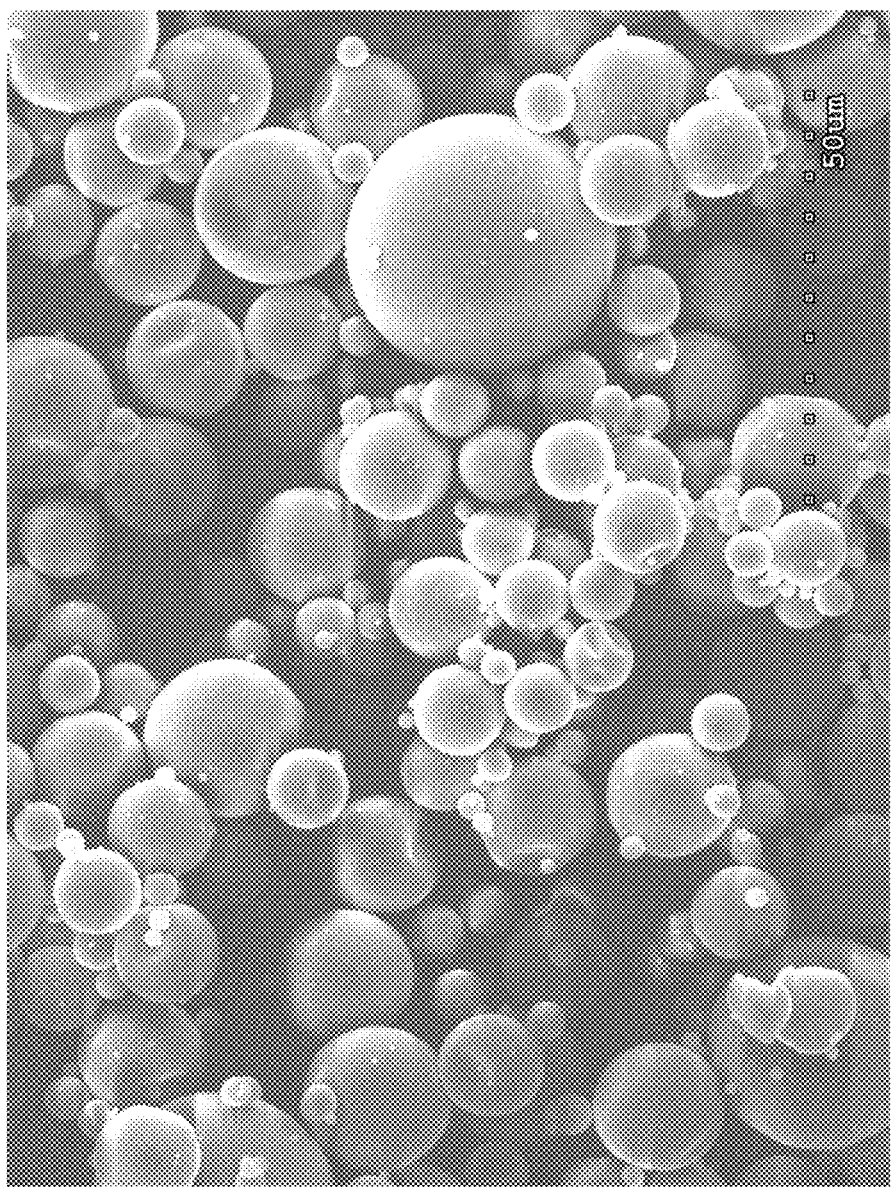
FIG. 3 is an SEM image, 50 μm scale, of microcapsules having a core encapsulated by a polymer wall prior to the addition of an exterior shell.

Referring to FIGS. 1 and 2, capsules 100c and 100d each have an outer shell 106, an inorganic shell, surrounding a polymer wall 104 encapsulating a core composition 102. The shell 106 is typically an outermost shell, but in some embodiments the shell 106 may have an exterior coating applied thereto after formation. The capsules 100c and 100d begin as pre-formed capsules 100 that have a core composition 102 encapsulated within a polymer wall 104. An SEM image of one embodiment of pre-formed capsules is included as FIG. 3. It is noted that the capsules are generally spherical capsules and based on their size are referred to as microcapsules.

With reference to FIG. 1, the shell 106 is connected to an exterior surface 105 of the polymer wall 104 of the pre-formed capsule 100 by a surfactant 108, and has a cation 110 attracted to the surfactant 108 and an anion or an anion equivalent 112 chemically bonded to the cation to form a solid precipitate (i.e., the shell 106). The shell 106 may be a continuous shell (i.e., a full, endless shell) or a discontinuous (partial) shell. The shell 106 is deposited onto the capsules, held there by the surfactant.

Figure 6:
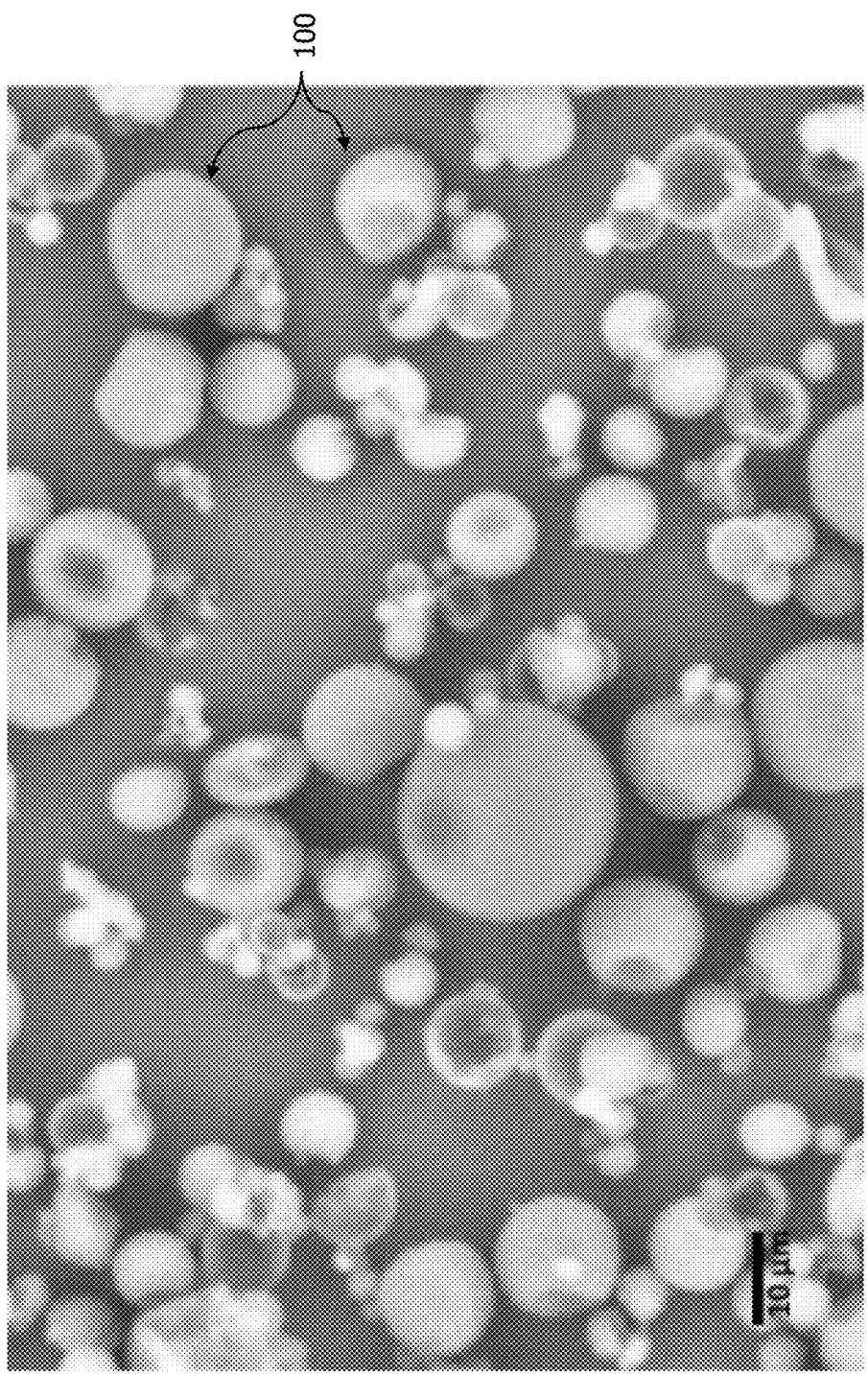
FIG. 6 is an SEM image, 10 μm scale, of a plurality of boehmite coated microcapsules containing a carboxylic acid core made per the shell formation process of FIG. 1.

With reference to FIG. 2, in an alternate process, the shell 106 is connected to an exterior surface 105 of the polymer wall 104 of the pre-formed capsule 100 by a surfactant 108, and has a metal-containing compounding 113 attracted to the surfactant 108 to form a solid shell 106. The shell 106 may be a continuous shell or a discontinuous shell. An example of a discontinuous, crystalline shell is shown in the SEM images of FIG. 6. Here, the core of the final capsule 100d comprises dodecanoic acid and the shell 106 comprises boehmite (an aluminum oxide hydroxide mineral). The shell 106 is deposited onto the capsules, held there by the surfactant.

Synthesis of the dual reagent mono-microcapsules is carried out in the following way. First, the liquid core component, usually an oil or a wax, is mixed together with water and a surfactant at a temperature above the material's melting point and stirred until a stable emulsion forms. Then, the desired size of the capsules in the emulsion is obtained with a homogenizer, and the wall materials are added sequentially. The newly formed microcapsules are then cured at 65-85° C. for 4-8 hours, then cooled to ambient temperature. Then, the pre-formed microcapsules are washed via vacuum filtration, and re-suspended in water for application of the second reagent to the outer wall. A surfactant is applied to the outer wall of the capsules, then the second reagent is tethered to the surfactant through electrostatic interactions, either through the cation-anion process of FIG. 1 or the metal compound process of FIG. 2. The dual reagent mono capsules are then washed several times and filtered.

Figure 5:
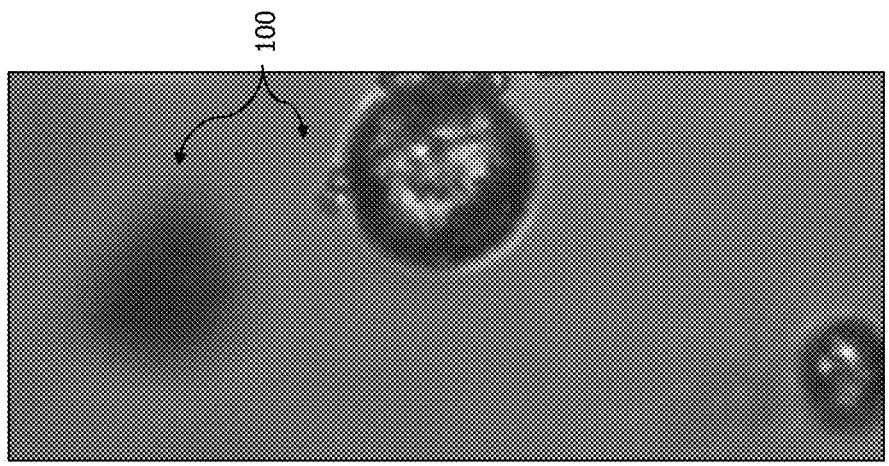
FIG. 5 is a microscopic image at 60 times magnification of the boehmite coated microcapsules of FIG. 3.
Figure 4:
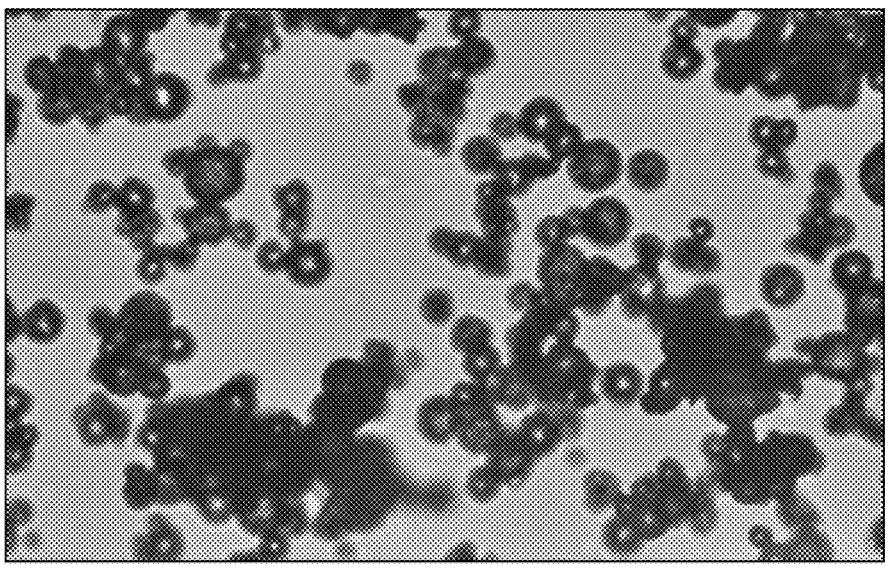
FIG. 4 is a microscopic image, at 10 times magnification, of boehmite coated microcapsules containing a carboxylic acid core made per the shell formation process of FIG. 1.

Often times, the secondary reagent is an inorganic compound. Because inorganic compounds form crystalline structures rather than continuous films, the secondary reagent on the surface of the capsules is often seen as a rough, granular layer, which is demonstrated in FIG. 6 and described above as being generally a discontinuous shell. Additional images of the dodecanoic-boehmite mono-microcapsules are provided in FIGS. 4 and 5 at different magnifications.

Figure 7:
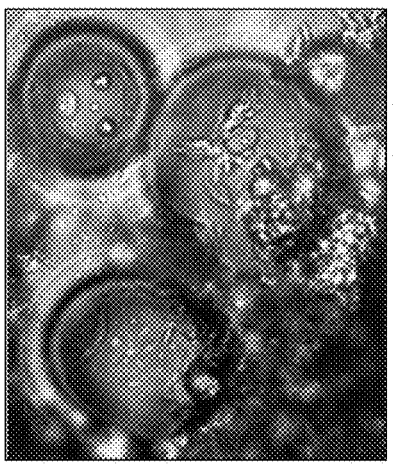
FIGS. 7 and 8 are microscopic images of boehmite coated microcapsules at 60 times magnification at a rupture time $T_0$.
Figure 8:
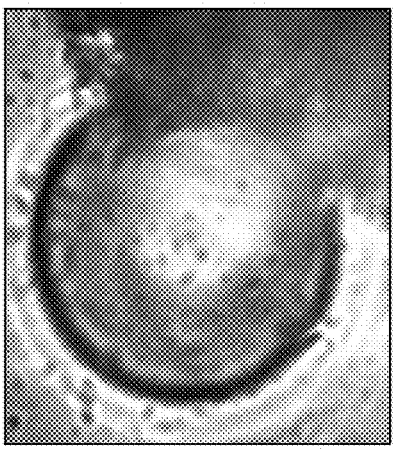
Figure 9:
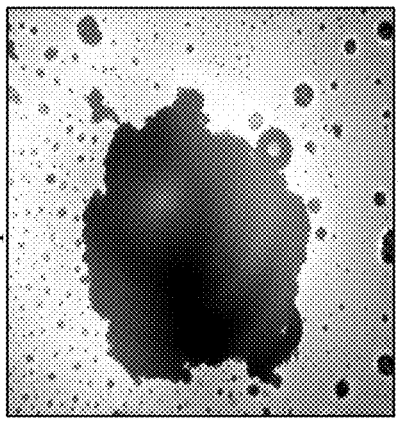
FIG. 9 is a microscopic image of boehmite coated microcapsules at 40 times magnification at a rupture time $T_4$.
Figure 10:
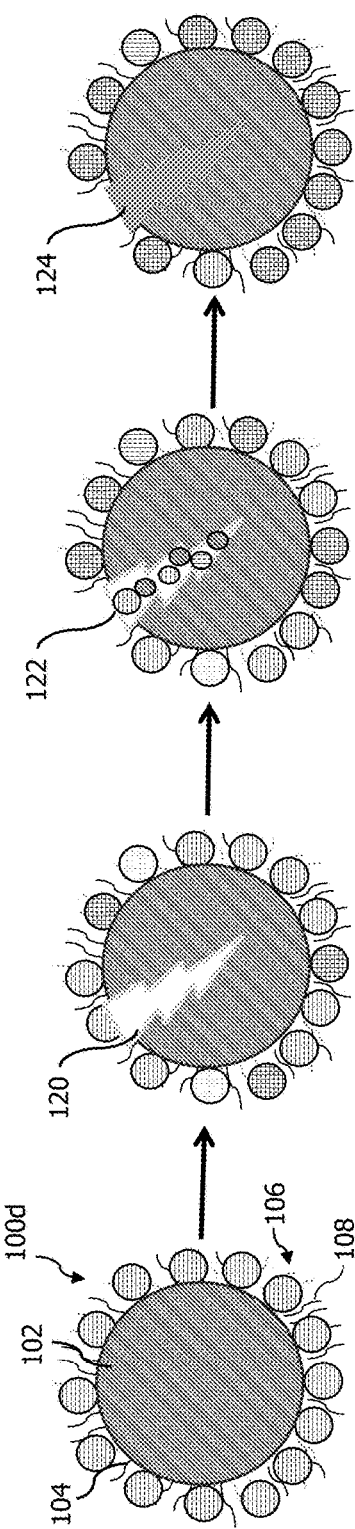
FIG. 10 is a schematic illustration of the rupture and dual reagent chemical reaction resulting in a self-healed microcapsule.

Now turning to FIGS. 7-10, images and a schematic representation of the dodecanoic-boehmite mono-microcapsules 100d upon rupture 120 of the microcapsules are shown. When the microcapsules rupture, the reagent in the core contacts the reagent on the exterior surface 122 of the capsules, a chemical reaction occurs that produces a reaction product 124 that fills in the crack produced by the rupture or that fills in a crack or mar in the surface to which the microcapsules were applied, such as the surface of a ship or beam of a bridge, etc. This chemical reaction is shown in FIGS. 7 and 8 at 60× magnification at the initial rupture of the microcapsules. FIG. 9 is the chemical reaction at 40× magnification four hours after the initial rupture of the capsules (i.e., $T_4$), demonstrating how much reaction product is formed and obscuring the original microcapsule. Here, the reaction product is carboxylate-alumoxane, which is a self-healing material. Typically, the resulting carboxylate-alumoxane has a curing time of 2-5 hours, which is ideal for the material to flow into and fix a crack or mar on a surface. The carboxylate-alumoxane is stable up to 350° C., is cheap to produce, and is insoluble in aqueous solutions, which is ideal for use in pipe coatings, in steel beams that are underwater, and on the exterior of ship hulls.

The rupture of the polymer wall may be by any means, such as mechanical or chemical means, for example, a scraping or marring of a surface or as a result of a pH change.

Based on the above description and working examples 1-5, the core composition 102, in one embodiment, comprises a carboxylic acid. The carboxylic acid is preferably one that reacts with a metal-containing compound to form a self-healing reaction product. Example carboxylic acids include decanoic acid, dodecanoic acid, heptadecanoic acid, tetradecanoic acid, palmitic acid, stearic acid, octanoic acid, and combinations thereof.

In another embodiment, the core composition 102 comprises a drying oil, in particular an oil that cures upon exposure to air, especially in the presence of a catalyst, such as an inorganic compound. Encapsulating the drying oil within a microcapsule as disclosed herein postpones curing of the oil until the capsules are broken and the oil is exposed to air. An inorganic compound, for example, one having a $Ca^{+2}$, $Mg^{+2}$, $Ag^{+1}$, $Co^{+2}$, $Co^{+3}$, $Ni^{+2}$, $Cu^{+1}$, $Cu^{+2}$, $Fe^{+2}$, $Fe^{+3}$, $Mn^{+2}$, $Ag^{+1}$, $Zn^{+2}$, $Al^{+3}$, and $B^{+3}$ cation forming part of an inorganic solid on the exterior of the polymer wall of the microcapsules, tethered thereto by a surfactant, acts as a catalyst in the curing process of the oil. Suitable oils include tung oil, linseed oil, poppy oil, walnut oil, sunflower oil, safflower oil, and combinations thereof. In another example embodiment, the core composition comprises tung oil and the shell material is an iron catalyst, copper catalyst, or a manganese catalyst.

In another embodiment, the core composition comprises an epoxide, such as Epon 828, and the shell material comprises an amine, such as diethylene triamine (DETA), wherein the amine is one that polymerizes the epoxide once the capsules are ruptured. Other amines can be used to cure Epon 828 such as triethylenetetramine, cycloaliphatic amines, amindoamines, metaphenylenediamine, methylene dianiline, and diaminodiphenyl sulfone.

The pre-formed capsules 100 and the resultant capsules 100c, 100d can be microcapsules or macrocapsules, which will typically have a relatively high payload of the core material relative to the amount of material forming the shell or capsule wall. The payload of core material in any of the capsules may be about 10% to about 90% by weight, preferably at least 50%, more preferably at least 70%, and even more preferably at least 80%. In any of the capsules made by the methods disclosed herein, the payload of core material may be about 70% to about 80% by weight, more preferably about 75% to about 85%, and even more preferably about 77% to about 81%.

The size of the resultant capsules 100c, 100d can vary depending upon the size of the pre-formed capsules 100 used and the amount of shell material deposited on the polymer wall 104 of the pre-formed capsules 100. A microcapsule is typically one having a diameter in the range from about 1 μm to about 1000 μm. Microcapsules useful in the applications discussed herein more typically have a diameter from about 10 μm to about 600 μm. The capsule diameter selected depends upon a user's intended application or use for the capsules.

The pre-formed capsules 100 have a polymer wall 104, which may comprise melamine formaldehyde, gelatin, a cross-linked melamine, acrylic polymer, or other known wall material made using known methods such as in-situ polymerization, interfacial polycondensation, interfacial cross-linking, or any other known method. Melamine-formaldehyde (MF) capsules can be prepared by the in-situ polymerization process of polycondensation, where the melamine-formaldehyde prepolymer is initially soluble in the continuous water phase, while a hydrophobic core material is contained in dispersed droplets. As the polymerization reaction starts in the aqueous solution, the formed oligomers start to collapse on the surface of the core droplets. On the surface, the polymerization continues and crosslinking occurs, which results in the formation of a solid MF wall.

Capsules having a gelatin wall encapsulating a core material are known, as taught in Onder et al. *Encapsulation of Phase Change Materials by Complex Coacervation to Improve Thermal Performances of Woven Fabrics*, Thermochimica Acta. 2008, 467, 63-72, and in Patrick et al. *Optimization Process by Complex Coacervation of Fish Oil Using Gelatin/SDS/NaCMC and Secondary Coating Application with Sodium Polyphosphate*, IJSBAR. 2014, 17, 74-94.

For a cross-linked melamine microcapsule, reference is made to co-pending U.S. application Ser. No. 15/420,435 for methods of making the microcapsule, which is incorporated herein by reference. These microcapsules are made from a melamine formaldehyde prepolymer comprising a crosslinking agent, the crosslinking agent being a mixture of:

(a) a reaction product of a cyclic urea (U) and a multifunctional aldehyde (A), and (b) at least one crosslinker selected from the group consisting of (b1) reaction products of an aminotriazine and at least one aldehyde selected from the group consisting of aliphatic monoaldehydes and multifunctional aliphatic aldehydes having the structure Y(CH)$_n$, where Y is an n-functional aliphatic residue, and n is greater than 1, where U is not dihydroxyethylene urea if the crosslinker (b) is (b1), (b2) reaction products of urea and/or cyclic ureas and formaldehyde, (b3) alkoxycarbonylaminotriazines, (b4) multifunctional isocyanates which may be partially or completely blocked, (b5) reaction products of phenols and aliphatic monoaldehydes, (b6) multifunctional epoxides, (b7) multifunctional aziridines, (b8) multifunctional carbodiimides, wherein any of the crosslinkers (a) and (b) which have hydroxyl groups may be etherified with one or more linear, branched, or cyclic aliphatic alcohols, polymerized by adjusting the pH and/or addition of urea. The crosslinking agent (b) is preferably at least one crosslinker selected from the group consisting of (b1), (b2), (b3), and (b5). These cross-linked melamine microcapsules have MF prepolymer present in a ratio by weight percent to the crosslinking agent of 1:1 to 4:1, more preferably 1.5:1 to 3.75:1. These capsules have an initial free formaldehyde level of less than 100 ppm, more preferably less than 80 ppm, less than 60 ppm, and even more preferably less than 40 ppm. Such a crosslinking agent is available from Allnex USA Inc.

In one embodiment, the crosslinking agent has the reaction product of a cyclic urea U and a multifunctional aliphatic aldehyde (A), portion (a), in a mixture with one or more of (b1), (b2), (b3) and (b5). Mixtures of the reaction product of a cyclic urea (U) and a multifunctional aldehyde (A) and at least one of the crosslinkers (b) have a ratio of the mass of the reaction product to the mass of the crosslinker (b) (or to the sum of the masses of all crosslinkers (b)) from 1/99 to 99/1, preferably from 10/90 to 90/10, and more preferably from 30/70 to 70/30.

The multifunctional aldehyde A has the formula OHC—R'—CHO where R' may be a direct bond or a divalent radical which may preferably be a linear, branched or cyclic aliphatic radical and may have from one to twenty carbon atoms, both these options for R' leading to a divalent aldehyde having exactly two —CHO groups, or an aliphatic divalent radical which may be linear, branched or cyclic and may have from one to twenty carbon atoms, which radical carries at least one additional aldehyde group —CHO, which latter option leads to trivalent or polyvalent aldehydes having at least three aldehyde groups. Preferred aldehydes are divalent aliphatic aldehydes, particularly glyoxal, malonic dialdehyde, succinic dialdehyde, and glutaric dialdehyde. Especially preferred is glyoxal in an aqueous solution, as anhydrous solid which has to be cooled as its melting temperature is 15° C., or in the form of its dimer or trimer, optionally in solid hydrated form as dihydrates, or in the form of its addition products with sulfites or hydrogen sulfites which decompose under acidic conditions.

The cyclic ureas U which may be used according to the present invention have at least one unsubstituted amidic —NH group. These cyclic ureas are cycloaliphatic or bicycloaliphatic compounds having an element of the structure —NH—CO—NH— within a ring structure, the total number of ring atoms preferably being from 5 to 7 (ethylene urea, 1,2-propylene urea, 1,3-propylene urea, 1,4-butylene urea or tetramethylene urea). Particularly preferred is ethylene urea or a mixture comprising ethylene urea, especially a mixture comprising at least a mass fraction of 50% of ethylene urea. In the case of a bicyclic compound, the simplest structure is glycoluril or acetylene diurea. Hydroxy functional ureas are not useful for the present invention. The cyclic ureas may be substituted, preferably by alkyl groups on the N- or C-atoms, or both, the alkyl residues preferably having from one to four carbon atoms. At least one of the nitrogen atoms must remain unsubstituted to enable reaction with the aldehyde functional molecule. Preferably, at least one cyclic urea is selected from the group consisting of ethylene urea, 1,2-propylene urea, hydantoin also known as glycolyl urea, and parabanic acid also known as oxalyl urea, and glycoluril. A particularly preferred combination is glyoxal reacted with ethylene urea, and optionally, either glyoxal, or ethylene urea, or both, in mixture with other multifunctional aldehydes and/or other cyclic ureas. In a preferred case of using ethylene urea as the cyclic urea, and glyoxal as the multifunctional aldehyde, —R'— is a direct bond, and —X— is —NH—CH$_2$—CH. Additional details are found in the co-pending application referenced above.

A melamine formaldehyde resin particularly suitable for the above cross-linked melamine capsules is CYMEL® 385 melamine formaldehyde resin available from Allnex USA Inc. The melamine formaldehyde resin may be one that includes phenol, such as a resorcinol urea formaldehyde resin.

One example method of making microcapsules that have an acrylic polymer wall is disclosed in U.S. Patent Application Publication No. 2015/0158003, published Jun. 11, 2015, which is incorporated herein by reference.

The surfactant 108 used to tether the shell 106 to the polymer wall 104 comprises an ionic surfactant. In one embodiment, the ionic surfactant may be mixed with a nonionic surfactant. The surfactant can affect the size and stability of the inorganic coated capsules as agglomeration can occur with some surfactant/shell system combinations and the stability of the shell. For example, an inorganic shell may detach from the polymer wall of the capsule 100 at a temperature of about 200° C. if it is not well bonded thereto. Most capsule walls are stable up to and about 300° C. to about 400° C.; thus, degradation at 200° C. is indicative that the surfactant is not tethering the metal to the polymer surface of the capsule.

Cationic surfactant can include, for example, amine salts, such as, ethoxylated tallow amine, cocoalkylamine, and oleylamine, quaternary ammonium compounds such as cetyl trimethyl ammonium bromide, myristyl trimethyl ammonium bromide, stearyl dimethyl benzyl ammonium chloride, lauryl/myristryl trimethyl ammonium methosulfate, stearyl octyldimonium methosulfate, dihydrogenated palmoylethyl hydroxyethylmonium methosulfate, isostearyl benzylimidonium chloride, cocoyl benzyl hydroxyethyl imidazolinium chloride, cocoyl hydroxyethylimidazolinium, or a mixture thereof. In some embodiments, the cationic surfactant is cetyl trimethyl ammonium bromide.

Suitable anionic surfactant include, but are not limited to, water-soluble salts of alkyl sulfates, alkyl ether sulfates, alkyl isothionates, alkyl carboxylates, alkyl sulfosuccinates, alkyl succinamates, alkyl sulfate salts such as sodium dodecyl sulfate, alkyl sarcosinates, alkyl derivatives of protein hydrolyzates, acyl aspartates, alkyl or alkyl ether or alkylaryl ether phosphate esters, sodium dodecyl sulphate, phospholipids or lecithin, or soaps, sodium, potassium or ammonium stearate, oleate or palmitate, alkylarylsulfonic acid salts such as sodium dodecylbenzenesulfonate (SDBS), sodium dialkylsulfosuccinates, dioctyl sulfosuccinate, sodium dilaurylsulfosuccinate, poly(styrene sulfonates) and salts thereof, isobutylene-maleic anhydride copolymer, gum arabic, sodium alginate, carboxymethylcellulose, cellulose sulfate and pectin, isobutylene-maleic anhydride copolymer, carrageenan; semi-synthetic polymers such as sulfated methylcellulose, carboxymethyl starch, phosphated starch, lignin sulfonic acid; and synthetic polymers such as maleic anhydride copolymers (including hydrolyzates thereof), polyacrylic acid, polymethacrylic acid, acrylic acid butyl acrylate copolymer or crotonic acid homopolymers and copolymers, vinylbenzenesulfonic acid or 2-acrylamido-2-methylpropanesulfonic acid homopolymers and copolymers, and partial amide or partial ester of such polymers and copolymers, carboxymodified polyvinyl alcohol, sulfonic acid-modified polyvinyl alcohol and phosphoric acid-modified polyvinyl alcohol, phosphated or sulfated tristyrylphenol ethoxylates.

Example nonionic surfactants include, but are not limited to, ethylene maleic anhydride (EMA), sorbitan stearate (e.g., SPAN® 60), sorbitan monooleate (e.g., SPAN® 80), polyethylene glycol sorbitan monooleate (TWEEN® 80), polyvinyl alcohol, ethylene oxide/propylene oxide block copolymers (e.g., PLURONIC® P105), polyoxyethylene (5) nonylphenylether, branched (IGEPAL® CO-520), or a mixture thereof.

If the scheme set forth in FIG. 1 is utilized, the cation 110 attracted to the surfactant is a metal ion such as $Ca^{+2}$, $Mg^{+2}$, $Ag^{+1}$, $Co^{+2}$, $Co^{+3}$, $Ni^{+2}$, $Cu^{+1}$, $Cu^{+2}$, $Fe^{+2}$, $Fe^{+3}$, $Mn^{+2}$, $Zn^{+2}$, $Al^{+3}$, and $B^{+3}$, $Sn^{+2}$, $Sn^{+4}$, $Cr^{+2}$, $Cr^{+3}$, but is not limited thereto. The anion 112 for forming the shell 106 is one that is insoluble in water when paired with the cation 110. Suitable anions include, but are not limited to, one or more of $CO_3^{-2}$, $HPO_4^{-2}$, $PO_4^{-3}$, $SO_4^{-2}$, $SO_3^{-2}$, $OH^{-1}$, $H_2PO_4^{-1}$, $HSO_4^{-1}$, and $HSO_3^{-1}$, $CrO_4^{-2}$, $MnO_4^{-2}$, $S_2O_3^{-2}$. The anion equivalent is also insoluble in water when paired with the cation 110. Suitable anion equivalent includes graphene oxide, amines, and carboxylates. Some example amines include primary amines such as diethylenetriamine (DETA) and diethylamine (DEA). Some examples of carboxylates include octadecanoate ions, dodecanoate ions, and hexadecanoate ions.

Referring to FIGS. 1 and 2, the outer shell 106 is deposited onto the existing polymer wall of microcapsules 100 in an aqueous solution at temperatures between about 20° C. to about 70° C. As discussed above, the polymer wall 104 of microcapsules 100 may be, but are not limited to, organic polymers, cross-linked melamine (CM), and acrylic walls. In preferred embodiments, and those used in the working examples, the average capsule size (diameter) for the pre-formed capsules 100 ranges from about 2 μm to 85 μm. The polymer wall 104 is used as a scaffold in which a surfactant 108 can be applied, where the surfactant 108 tethers the outer shell 106 to the exterior surface 105 of the polymer wall 104. Either ionic or nonionic surfactants can be used, but ionic surfactants are preferred. The surfactant 108 is dissolved in water, typically deionized water, which may be warmed. The surfactant solution typically has a concentration of about 0.5% to about 3% by weight relative to the weight of pre-formed capsules selected for the batch. The pre-formed capsules 100 are added to the surfactant solution (or vice versa) with stirring for sufficient time to allow the surfactant 108 to tether to the polymer wall 104 thereof, thereby forming intermediate capsules 100a.

After the surfactant 108 is applied to the polymer wall 104, if following the scheme of FIG. 1, a solution of metal cations 110 ($X^+$) is added dropwise into the aqueous solution of intermediate capsules 100a, preferably with stirring for a sufficient time to allow the cations to be associated/attracted to the surfactant. Before the dropwise addition, a metal compound that is soluble in water was dissolved in water, with heat if appropriate. The metal-containing solution comprised of 0.5% to about 25% by weight, more preferably about 1% to about 11% by weight, metal in deionized water was added dropwise to the surfactant-coated capsule-containing solution. The metal cations 110 are attracted to the surfactant 108 tethered to the exterior surface of the intermediate capsules 100a, thereby forming secondary intermediate capsules 100b.

Still referring to FIG. 1, in a separate container, the selected anion compound that is soluble in water is dissolved in water, typically with heating. The anion-containing solution is comprised of 0.5% to about 25% by weight, more preferably about 1% to about 13% by weight, metal in deionized water. This solution of anions 112 ($Y^-$) was added dropwise, in a similar manner to the addition of metal cation 110, to the solution of secondary intermediate PCM capsules 100b. The anion 112 must be insoluble in water with the previously added metal cation 112 in order to form a precipitated or deposited solid as a shell 106. After the anion 112 is added to solution, and enough time has been allowed for the shell 106 to form, the solution is filtered and washed several times in deionized water. The shell may comprise about 1% to about 10% by weight of each capsule, more preferably about 3% to about 8% by weight of each capsule.

Example 1

With reference to the scheme illustrated in FIG. 2, pre-formed microcapsules having a core composition comprising dodecanoic acid were provided. To tether the secondary reagent to the exterior surface of the polymer wall of the microcapsules, 2.5 g of a surfactant, such as cetyl trimethylammonium bromide (CTAB), was dissolved in 300 g of deionized water and heated to 40° C. Then, 25 g of the pre-formed microcapsules were added to this solution with mixing until the surfactant was bound to the capsule's polymer wall.

Separately, 15 g of boehmite was dissolved in 300 g of deionized water and heated to 40° C. Boehmite has the following chemical structure (I), which has aluminum within its structure that is or becomes available to associate with the surfactant tethered to the polymer wall of the preformed microcapsules.

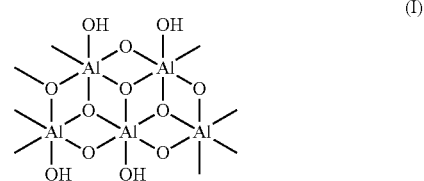

(I)

This boehmite solution was added dropwise to the solution containing the microcapsules with mixing until the aluminum was associated with (chemically connected to) the surfactant tethered to the microcapsules. The product was then washed several times in deionized water and vacuum filtered.

Example 2

The procedure of Example 1 was repeated, but the CTAB was replaced in turn with sodium dodecylbenzenesulfonate (SDBS), polyvinyl alcohol (PVA), SPAN™ 60 sorbitan esters with sodium dodecylbenzenesulfonate (SDBS), and ethylene maleic anhydride (EMA) with sodium dodecylbenzenesulfonate (SDBS). Microcapsules having an inorganic shell of alumoxane resulted from each trial. The general chemical structure of the alumoxane (II) is shown below.

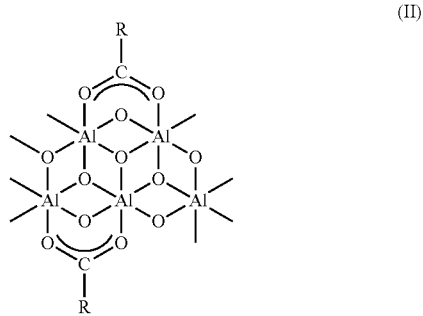

(II)

The preformed microcapsules may be made as a first part of any of the methods disclosed herein. Several examples are provided below demonstrating different polymer walls of the preformed microcapsules.

Example 3: Melamine Formaldehyde Microcapsules

In one exemplary synthesis, 176.72 g of a surfactant such as ethylene maleic anhydride/diethylamine (EMA/DEA) (containing 2.5% EMA, 1.1% DEA, and 96.4% water) is mixed with 200 g of water and heated to 57° C. with stirring using an overhead mixer equipped with a turbine. Then, 241 g of a core material, here dodecanoic acid containing a 15% diluent such as octadecane, was added to the aqueous mixture of surfactant. A pH was maintained that was complementary to the core material. The pKa of dodecanoic acid is 4.9, so the pH of the surfactant solution was kept below 4.9 to avoid deprotonation of the core material. Upon addition of the core material, the stir speed was increased to about 300 rpm, and soon thereafter, a coacervate formed. After stir emulsifying for about an hour, wall materials were added.

In this example, the wall was a melamine formaldehyde (MF), in particular CYMEL® 385 resin. About 59 g of CYMEL® 385 resin was added to the core and surfactant coacervate, where 75% of the wall material was added 60 minutes after stir emulsifying, and the remaining wall material was added 70 minutes after stir emulsifying and homogenizing. After the first amount of wall material is added, the coacervate solution is homogenized to about 1 μm to about 100 μm diameter, more preferably about 10 μm to about 40 μm diameter microcapsules, and even more preferably about 15 μm to 25 μm diameter microcapsules using a homogenizer, for example one made by IKA Works, Inc. of Wilmington, N.C. Then, 25 minutes after the first CYMEL® 385 resin addition, 80 g of a salt solution such as potassium dihydrogen phosphate ($KH_2PO_4$) was added over 10 minutes. After the addition of the salt solution, the temperature of the solution was slowly raised to 85° C. Once the temperature was at 85° C., 16 g of urea was added, and the now formed microcapsules are allowed to cure at this temperature. After curing for 4 hours, the microcapsules were cooled to ambient temperature, the pH adjusted to 7 followed by vacuum filtering to recover the microcapsules.

Example 4: Resorcinol Urea Formaldehyde Microcapsules

In one exemplary synthesis of a resorcinol urea formaldehyde (RUF) microcapsule, 160 g of a surfactant such as polyvinyl alcohol (PVA) (containing 50% PVA-540 solution and 50% PVA-125 solution, where both contain 5% solids and 95% water) is mixed with 150 g water and heated to 45° C. with stirring using an overhead mixer equipped with a mixer turbine. Then, 148 g of a core material such as dodecanoic acid, previously heated to 50° C., was added to the aqueous mixture of surfactant. Upon addition of the core material, the stir speed was increased to about 300 rpm, and soon thereafter, a coacervate formed. After stir emulsifying for about an hour, the size of the capsules was obtained using a homogenizer, such as one made by IKA Works, Inc. of Wilmington, N.C. The size of the microcapsules ranges from about 1 μm to about 100 μm in diameter, more preferably about 10 μm to about 40 μm in diameter, and even more preferably about 15 μm to 25 μm in diameter. After the pre-selected diameter size was reached, the wall materials were added sequentially.

The wall material additions were: 6 g of urea, 11 g of resorcinol, 35 g of formaldehyde, and 80 g of water. The additions were made to the core and surfactant coacervate, where 33.3% of the wall material was added 60 minutes after stir emulsifying, 33.3% was added 60 minutes after the first wall addition, and the remaining wall material was added 120 minutes after the first wall addition. All wall materials were added to the coacervate dropwise. Furthermore, after the first wall addition, the pH of the emulsion was adjusted to be within the range of 1.5 to 2. After the last wall material was added, the temperature of the solution was raised to 50° C. and cured at this temperature for eight hours. After curing, the microcapsules were cooled to ambient temperature, the pH adjusted to 6 followed by vacuum filtering to recover the microcapsules.

Examples 3 and 4 were repeated with different carboxylic acids as the core materials, specifically, palmitic acid, stearic acid, heptadecanoic acid, and tetradecanoic acid, which were then treated according to the procedure of Example 1 to add an inorganic second reagent shell tethered to the polymer wall of the microcapsules by a surfactant.

Example 5

Figure 11:
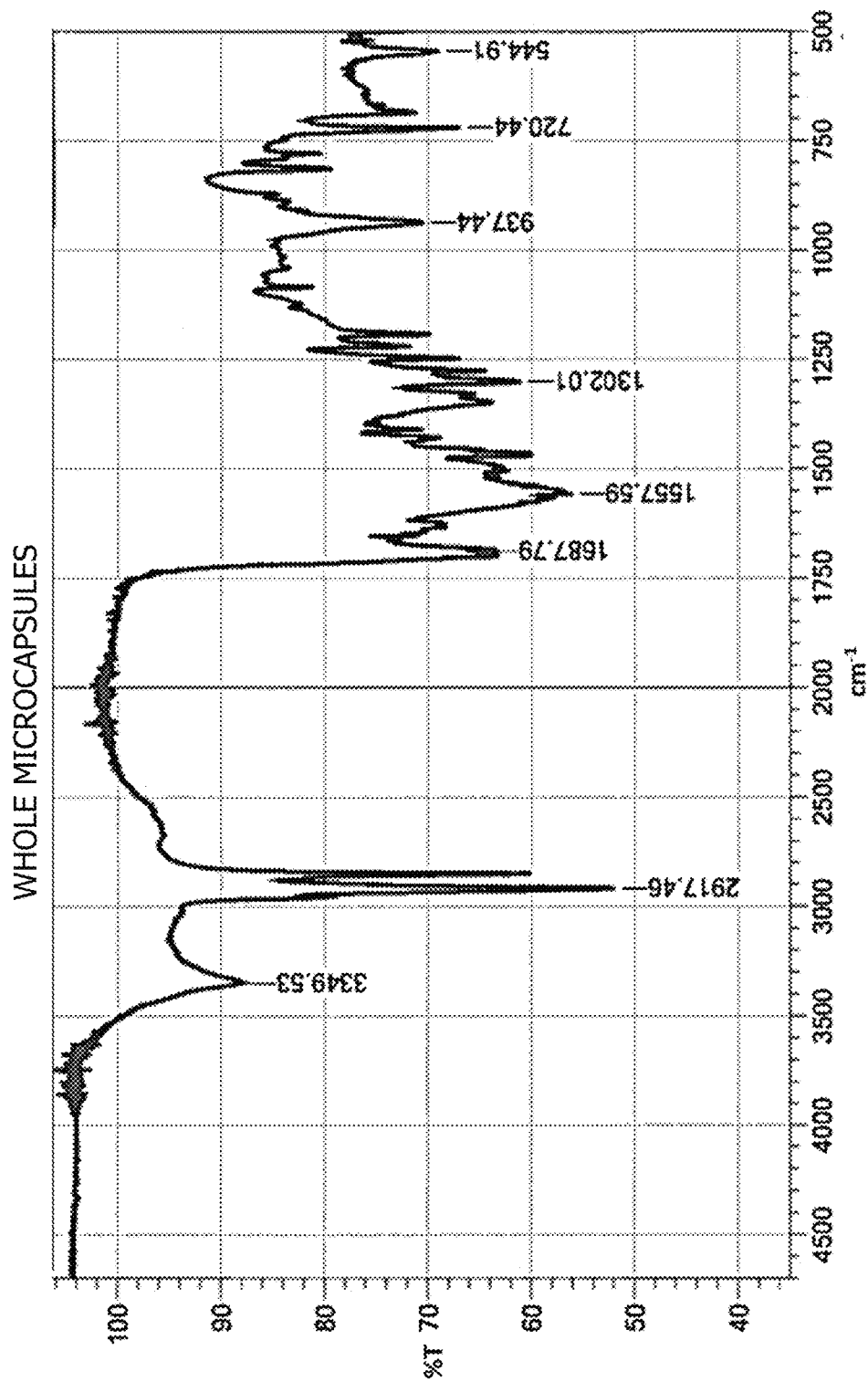
FIG. 11 is an FTIR image of an intact boehmite coated microcapsule.
Figure 12:
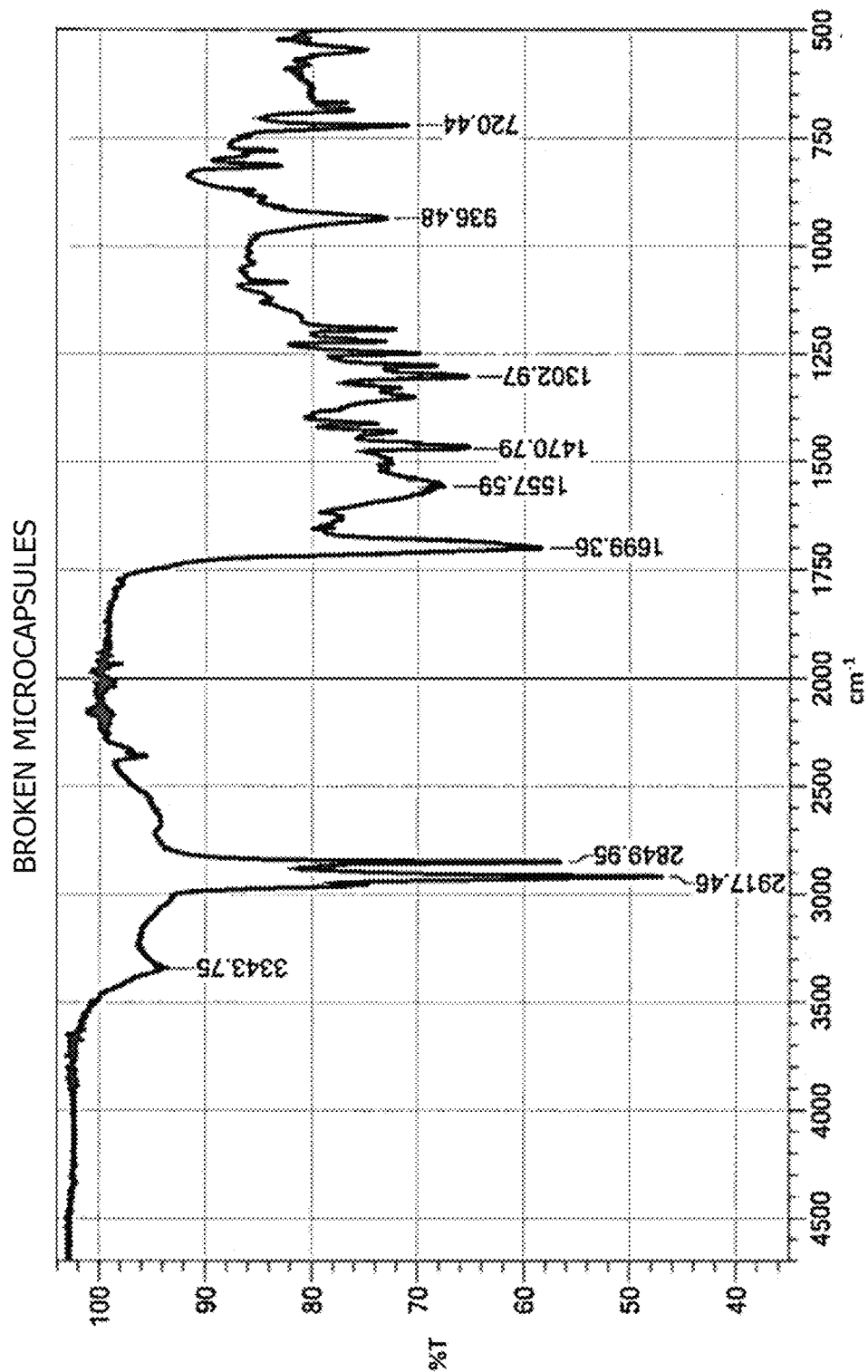
FIG. 12 is an FTIR image of a boehmite coated microcapsule after rupture.

FTIR images of the dual reagent capsules of Example 1 were determined (1) before rupture (whole microcapsules), and (2) after rupture. The FTIR images are included as FIGS. 11 and 12. Differences between the two FTIR images are found near 3300 cm$^{-1}$ and 1690 cm$^{-1}$, which indicate that a chemical reaction occurred. These capsules originally contain a carboxylic acid core, decanoic acid, where the reflection at 3349.53 cm$^{-1}$ in FIG. 11 indicates an O—H stretch, and the reflection at 1687.79 cm$^{-1}$ indicates at C=O stretch (i.e., a carboxylic acid is present). After the capsules rupture, the core (carboxylic acid) is exposed to the second reagent shell, boehmite (alumoxane), to react therewith. As seen in FIG. 12, the O—H stretch decreases significantly as well as shifts to a lower wavenumber, 3343.75 cm$^{-1}$. Furthermore, the C=O stretch increases to 1699.36 cm$^{-1}$. Both of these changes imply that the original carboxylic acid core has now become a carboxylate-alumoxane reaction product.

Example 6

The procedures of Examples 3 and 4 are equally suitable for encapsulating an oil, such as tung oil, linseed oil, poppy oil, walnut oil, sunflower oil, and/or safflower oil, as a first reagent core material to make the preformed microcapsules that will subsequently receive an exterior inorganic shell comprising a second reagent, here a metal compound that is suitable as a catalyst for a curing reaction of the oil when exposed to air.

Example 7

The preformed microcapsules from Example 6 are treated as follows to form the inorganic shell about the exterior surface thereof. 2.5 g of an ionic surfactant, sodium dodecylbenzenesulfonate (SDBS), was dissolved in 400 g of deionized water and heated to 34° C. 50 g of the preformed microcapsules were added to the solution of SDBS with stirring until the surfactant was associated to the surface of the capsule wall, thereby forming intermediate microcapsules. Separately, 22 g of calcium chloride ($CaCl_2$) was dissolved in 600 mL of deionized water and heated to 40° C. The $CaCl_2$ solution was added dropwise to the solution of intermediate microcapsules with stirring until the metal was associated with the surfactant on the surface of the capsules, thereby forming secondary intermediate microcapsules according to the schematic illustration provided in FIG. 1. In a separate container, 21 g of sodium carbonate ($Na_2CO_3$) was dissolved in 500 mL of deionized water and heated to 40° C. The $Na_2CO_3$ solution was added dropwise to the solution of secondary intermediate microcapsules. The entire solution was allowed to stir until the precipitation of $Ca_2CO_3$ formed the inorganic shell about each preformed microcapsule. The product was then filtered and washed several times in deionized water.

Example 7 was repeated with combinations of the following cations and anions: $Ca^{+2}$, $Mg^{+2}$, $Ag^{+1}$, $Co^{+2}$, $Co^{+3}$, $Ni^{+2}$, $Cu^{+1}$, $Cu^{+2}$, $Fe^{+2}$, $Fe^{+3}$, $Mn^{+2}$, $Ag^{+1}$, $Zn^{+2}$, $Al^{+3}$, and $B^{+3}$, as well as $CO_3^{-2}$, $HPO_4^{-2}$, $PO_4$-3, $SO_4^{-2}$, $SO_3^{-2}$, $OH^{-1}$, $H_2PO_4^{-1}$, $HSO_4^{-1}$, and $HSO_3^{-1}$. Some exemplary combinations include, but are not limited to, $CaCO_3$, $CaHPO_4$, $Ca_3(PO_4)_2$, $Ca(H_2PO_4)_2$, $CaSO_4$, $CaSO_3$, $Ca(HSO_4)_2$, $MgCO_3$, $MgHPO_4$, $Mg_3(PO_4)_2$, $Mg(H_2PO_4)_2$, $Ag_2CO_3$, $Ag_3PO_4$, $Ag_2HPO_4$, $AgH_2PO_4$, $Ag_2SO_4$, $Ag_2SO_3$, and $AgHSO_4$, $Cu_3(PO_4)_2$, $CuHPO_4$, $CuCO_3$, $FeCO_3$, $Fe_3(PO_4)_2$, and $FeHPO_4$.

The advantage of the microcapsules described above is the accessibility between the first and second reagents. Since the second reagent is carried by the microcapsule, equality of dispersement in a coating is easily achieved, and as soon as the capsule is ruptured, the core reagent material, which is selected to be a liquid at the time of rupture, comes into contact with the reagent material tethered to the surface of the capsule. Accordingly, very precise reactions can be carried out within a small surface area coated with the microcapsules. These dual reagent mono-microcapsules have applications in areas such as self-healing materials, adhesives, security, textiles and dyes, and medical fields, but are not limited thereto. For example, a micro-crack that forms in a coating on a pipe can be healed by the reaction product of the two reagents upon rupture of the mono-microcapsules (the cause of the crack or the cracking process itself ruptures the mono-microcapsules), which forms before the crack is allowed to get any bigger and damage the pipe. This property of self-healing is attractive within the construction and marine industries, as repair of certain materials can be difficult, especially pipes or metal beams that are underwater.

The embodiments of this invention shown in the drawings and described above are exemplary of numerous embodiments that may be made within the scope of the appended claims. The scope of the patent issuing herefrom should be construed as limited only by the scope of the appended claims.

What is claimed is:

1. A ruptureable capsule comprising:
    a core composition encapsulated within a polymer wall, the core composition comprising a first reagent; and
    a shell connected to an exterior surface of the polymer wall by a surfactant, the shell comprising a second reagent attracted to the surfactant by a chemical electrostatic interaction in the form of a discontinuous shell;
    wherein, upon rupture of the polymer wall, the first reagent and the second reagent chemically react with one another to form a reaction product.

2. The capsule of claim 1, wherein the reaction product seals the rupture in the capsule or seals a feature of a surface upon which the capsules are disposed.

3. The capsule of claim 1, wherein the second reagent comprises a mineral containing a metal that is available for chemical attraction or bonding to the surfactant, and the first reagent is a carboxylic acid.

4. The capsule of claim 3, wherein the metal is selected from the group consisting of aluminum calcium, silver, magnesium, iron, copper, and cobalt, and combinations thereof.

5. The capsule of claim 3, wherein the metal is an aluminum.

6. The capsules of claim 1, wherein the second reagent is an inorganic compound and the shell connected to the exterior surface of the polymer wall by the surfactant is crystalline.

7. The capsule of claim 6, wherein the core composition comprises a natural oil, and the inorganic compound catalyzes a reaction of the natural oil.

8. The capsule of claim 1, wherein the surfactant comprises an ionic surfactant.

9. The capsule of claim 1, wherein the polymer wall comprises melamine formaldehyde, gelatin, cross-linked melamine, resorcinol urea formaldehyde, or acrylic polymer.

10. The capsule of claim 9, wherein the polymer wall comprises a cross-linked melamine and the core comprises a phase change material, the cross-linked melamine comprising melamine formaldehyde polymerized with a cross-linking agent comprising:
    (a) a reaction product of a cyclic urea (U) and a multifunctional aldehyde (A), and
    (b) at least one crosslinker selected from the group consisting of
        (b1) reaction products of an aminotriazine and at least one aldehyde selected from the group consisting of aliphatic monoaldehydes and multifunctional aliphatic aldehydes having the structure $Y(CHO)_n$, where Y is an n-functional aliphatic residue, and n is greater than 1, where U is not dihydroxyethylene urea if the crosslinker (b) is (b1),
        (b2) reaction products of urea and/or cyclic ureas and formaldehyde,
        (b3) alkoxycarbonylaminotriazines,
        (b4) multifunctional isocyanates which may be partially or completely blocked,
        (b5) reaction products of phenols and aliphatic monoaldehydes,
        (b6) multifunctional epoxides,
        (b7) multifunctional aziridines,
        (b8) multifunctional carbodiimides, wherein any of the crosslinkers (a) and (b) which have hydroxyl groups may be etherified with one or more linear, branched, or cyclic aliphatic alcohols.

11. A method for surface treating capsules, the method comprising:
   providing capsules comprising a core composition encapsulated within a polymer wall;
   mixing an aqueous surfactant and the capsules together, wherein the surfactant attaches to an exterior surface of the polymer wall to form a surfactant-capsule intermediate;
   adding a solution of an inorganic compound wherein a metal therein is available for association with the surfactant;
   mixing until the metal of the inorganic compound chemically bonds to the surfactant and forms a discontinuous outer shell on the polymer wall of the capsules.

12. The method of claim 11, further comprising forming the capsules before mixing with the aqueous surfactant.

13. The method of claim 11, wherein the surfactant comprises an ionic surfactant.

14. The method of claim 11, wherein the polymer wall comprises melamine formaldehyde, gelatin, cross-linked melamine, resorcinol urea formaldehyde, or acrylic polymer.

15. The method of claim 11, wherein the core composition comprises a natural oil, and the inorganic compound catalyzes a reaction of the natural oil.

16. The method of claim 11, wherein the core composition comprises a carboxylic acid and the inorganic compound chemically reacts with the carboxylic acid.

17. A self-healing material comprising:
   a delivery medium; and
   a plurality of ruptureable capsules comprising:
      a core composition encapsulated within a polymer wall, the core composition comprising a first reagent; and
      a shell connected to an exterior surface of the polymer wall by a surfactant, the shell comprising a second reagent attracted to the surfactant by a chemical electrostatic interaction in the form of a discontinuous shell;
      wherein, upon rupture of the polymer wall, the first reagent and the second reagent chemically react with one another to form a reaction product.

18. The self-healing material of claim 17, wherein the second reagent comprises a mineral containing a metal that is available for chemical attraction or bonding to the surfactant, and the first reagent is a carboxylic acid.

19. The self-healing material of claim 17, wherein the core composition comprises a natural oil, and the second reagent is an inorganic compound that catalyzes a reaction of the natural oil with air.

20. A ruptureable capsule comprising:
   a core composition encapsulated within a polymer wall, the core composition comprising a first reagent; and
   a shell connected to an exterior surface of the polymer wall by a surfactant, the shell comprising a second reagent attracted to the surfactant by a chemical electrostatic interaction;
      wherein, upon rupture of the polymer wall, the first reagent and the second reagent chemically react with one another to form a reaction product;
      wherein the polymer wall comprises a cross-linked melamine and the core comprises a phase change material, the cross-linked melamine comprising melamine formaldehyde polymerized with a crosslinking agent comprising:
(a) a reaction product of a cyclic urea (U) and a multifunctional aldehyde (A), and
(b) at least one crosslinker selected from the group consisting of
   (b1) reaction products of an aminotriazine and at least one aldehyde selected from the group consisting of aliphatic monoaldehydes and multifunctional aliphatic aldehydes having the structure $Y(CHO)_n$, where Y is an n-functional aliphatic residue, and n is greater than 1, where U is not dihydroxyethylene urea if the crosslinker (b) is (b1),
   (b2) reaction products of urea and/or cyclic ureas and formaldehyde,
   (b3) alkoxycarbonylaminotriazines,
   (b4) multifunctional isocyanates which may be partially or completely blocked,
   (b5) reaction products of phenols and aliphatic monoaldehydes,
   (b6) multifunctional epoxides,
   (b7) multifunctional aziridines,
   (b8) multifunctional carbodiimides,
wherein any of the crosslinkers (a) and (b) which have hydroxyl groups may be etherified with one or more linear, branched, or cyclic aliphatic alcohols.

* * * * *